United States Patent [19]

Longest, Jr. et al.

[11] Patent Number: 5,305,392
[45] Date of Patent: Apr. 19, 1994

[54] HIGH SPEED, HIGH RESOLUTION WEB INSPECTION SYSTEM

[75] Inventors: H. Cary Longest, Jr.; Robert H. Moffitt, both of Midlothian; W. Randolph Sweeney, Richmond, all of Va.

[73] Assignee: Philip Morris Incorporated, New York, N.Y.

[21] Appl. No.: 2,892

[22] Filed: Jan. 11, 1993

[51] Int. Cl.[5] ............................. G06K 9/00
[52] U.S. Cl. .............................. 382/8; 382/34
[58] Field of Search .............. 382/8, 34, 30; 358/106, 358/101; 356/430, 431; 250/571, 572, 563, 548

[56] References Cited

U.S. PATENT DOCUMENTS

| | | | |
|---|---|---|---|
| 3,835,332 | 9/1974 | Bridges | 250/563 |
| 4,675,730 | 6/1987 | Adomaitis et al. | 358/106 |
| 4,803,734 | 2/1989 | Onishi et al. | 382/34 |
| 4,828,156 | 5/1989 | Whiteley et al. | 226/1 |
| 4,866,288 | 9/1989 | Weber | 250/572 |
| 4,885,785 | 12/1989 | Reynolds et al. | 382/8 |
| 4,891,528 | 1/1990 | Kuecker et al. | 250/548 |
| 4,893,346 | 1/1990 | Bishop | 382/8 |
| 4,924,086 | 5/1990 | Weber | 250/235 |
| 4,932,065 | 6/1990 | Feldgajer | 382/9 |
| 4,952,062 | 8/1990 | Bean, III et al. | 356/430 |
| 4,974,261 | 11/1990 | Nakahara et al. | 382/22 |
| 4,975,971 | 12/1990 | Ohnishi | 382/8 |
| 4,975,972 | 12/1990 | Bose et al. | 382/8 |
| 5,046,111 | 9/1991 | Cox et al. | 382/8 |
| 5,065,440 | 11/1991 | Yoshida et al. | 382/34 |
| 5,113,454 | 5/1992 | Marcantonio et al. | 358/106 |
| 5,121,444 | 6/1992 | Takizawa et al. | 382/34 |
| 5,165,101 | 11/1992 | Cox et al. | 382/8 |

*Primary Examiner*—Leo H. Boudreau
*Assistant Examiner*—John B. Vigushin
*Attorney, Agent, or Firm*—Kevin B. Osborne; Charles E. B. Glenn; James E. Schardt

[57] ABSTRACT

A modular system and method using the system for the high speed high resolution inspection of printed webs are provided. Each module inspects one lane of a printed web for print defects. Each gray scale or bipolar gray scale gradient pixel value of a digitally converted input image is compared to the minimum and maximum threshold values of the image template by a real-time digital signal processor. The image template is created in a secondary non-real-time processor by producing a statistical representation of a number of input images. The image template is desensitized to longitudinal and transverse jitter of the printed web so that jitter is not identified by the system as a print defect. The user is signaled if actual print defects exist and the lanes in which the defects exist are identified.

10 Claims, 5 Drawing Sheets

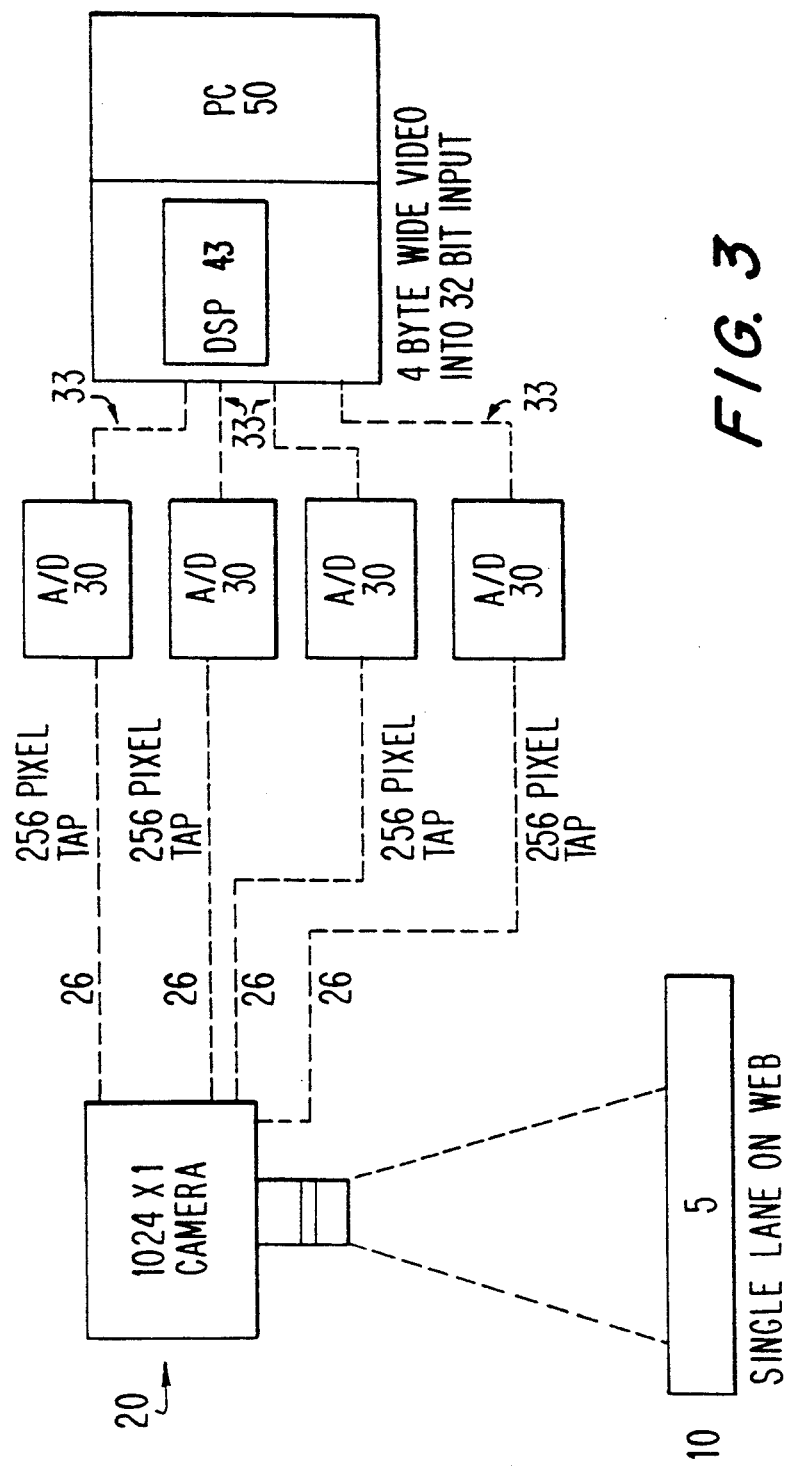

HIGH SPEED, HIGH RESOLUTION WEB INSPECTION SYSTEM

BACKGROUND OF THE INVENTION

The present invention relates to a system which permits high speed, high resolution inspection of printed webs.

In many industries packaging materials are printed at extremely high rates of speed up to 1200 feet per minute. Some automatic method of detecting flaws in the printed web must be employed since human inspectors cannot discern errors, other than gross errors, at such rates of speed. This invention permits the detection of misprinted areas in a printed web at the rate of speed of printing presses used in the printing of packaging for consumer products, for example cigarette packs.

It is known that flaws in webs of printed fabric can be detected by passing light through the fabric, sensing the light electrically, converting the amount of light sensed into a proportional voltage signal and then comparing the input to the standard signal for flawless fabric, as disclosed in U.S. Pat. No. 4,952,062. However, these types of systems do not operate at the high rates of speed needed in the packaging industries. Also, these systems do not provide a means for the detailed analysis of printed patterns on more opaque heavy coated paper stock web.

Inspection systems that convert the printed matter to video images, and then digitally process the video images, are also known. However, the difficulty of detecting flaws in images at such a high rate of speed is the amount of data generated for an entire image. The use of algorithms which detect flaws by comparing an entire image to a predetermined pattern requires too much processing power to be cost effective in a real-time operation.

A printed web which is 102.4 millimeters (or approximately 4 inches) wide would require 1 kilobyte (1024 bytes) of data per video scan line in order to detect flaws of 0.1 millimeter. Each 0.1 millimeter square could be considered one pixel. Each pixel requires 8 bits of binary data (1 byte) to represent the 256-level gray scale value assigned to describe the reflectivity of each pixel. At 500 feet per minute, 25,400 lines at a resolution of 0.1 millimeter pass every second. Therefore, the total data throughput at 500 feet per minute is approximately 25,400 kilobyts per second (24.8 megabytes per second). For complex pattern recognition algorithms, this rate of data throughput is too great to permit real-time recognition of flawed patterns with currently available cost effective technology.

Another difficulty with such web speeds is the inherent jitter of the web in both the longitudinal and transverse axes. Longitudinal jitter results from longitudinal movement of the web which is greater than the movement detected by the shaft encoder (i.e., a phase change between the web and the shaft encoder). This longitudinal "slipping" can occur due to wearing of the mechanical components of the web transport apparatus. Transverse jitter is the movement of the web perpendicular to the direction of movement of the web. Transverse jitter occurs due to the inherent difficulties in providing exact tolerances in a mechanical web printing apparatus. Such jitter causes the input image of the inspection system to be misaligned with respect to the target image resulting in incorrect flaw determinations.

In the consumer products packaging industries a flexible system is also required. Since label requirements are often dictated by marketing needs or federal and state administrative agencies, a system which is easily trained to detect flaws in different label configurations is necessary. In the cigarette industry the four Surgeon General's warning labels rotate on a quarterly basis. Reprogramming, or "training", of a web inspection system to accommodate changes in the printed matter must be reduced to a minimum to deal with such frequent changes.

It would be desirable to provide a web inspection system which is capable of high speed inspection of webs to provide for the real-time detection of flaws in printed webs produced at high speeds—e.g., up to about 1200 feet per minute.

It would also be desirable to provide a web inspection system capable of being trained quickly and easily on different image sets.

Furthermore, it would be desirable to provide a web inspection system which is capable of minimizing the effect of misalignment of input images due to jitter in the longitudinal and transverse axes.

It would further be desirable to provide a web inspection system that accepts or rejects inspected webs based on statistical rules ascertained through prior inspections.

Finally, it would be desirable to provide a web inspection system which is an expandable modular design using cost-effective available hardware.

SUMMARY OF THE INVENTION

It is an object of this invention to provide a web inspection system which is capable of real-time detection of flaws in printed webs which are produced at high speeds—e.g., up to about 1200 feet per minute.

It is also an object of this invention to provide a web inspection system which can be trained quickly and easily to detect flaws in different image sets.

Furthermore, it is an object of this invention to provide a web inspection system that is capable of minimizing the effect of misalignment of input images due to jitter in the longitudinal and transverse axes.

A further object of the invention is to provide a web inspection system that accepts or rejects inspected webs based on statistical rules ascertained through prior inspections.

Finally, it is an object of this invention to provide a web inspection system that is a modular combination of cost-effective available hardware which can be adapted to webs of differing widths.

In accordance with this invention, there is provided a modular web inspection system having an analog input means, analog-to-digital conversion means, primary real-time digital signal processing means and secondary non-real-time processing means, said system allowing the input of an analog representation of each pixel of a line of a printed web, the conversion of the analog representation to a gray scale digital representation, the transferring of the digital representation of each line to the digital signal processing means, the further transferring of the digital representation of a collection of lines comprising an image to the secondary processing means, the creation of a statistical representation of the gray scale values for each pixel, the calculation of the minimum and maximum threshold values to create a jitter desensitized template, the transferring of the template to the digital signal processing means and the comparison of the input images to that template.

BRIEF DESCRIPTION OF THE DRAWINGS

The above and other objects and advantages of the invention will become apparent upon consideration of the following detailed description, taken in conjunction with the accompanying drawings, in which like reference characters refer to like parts throughout, and in which:

FIG. 3 is a block diagram of a second embodiment of a web inspection module according to the invention for use in the modular web inspection system of FIG. 1;

DETAILED DESCRIPTION OF THE INVENTION

Figure 1:
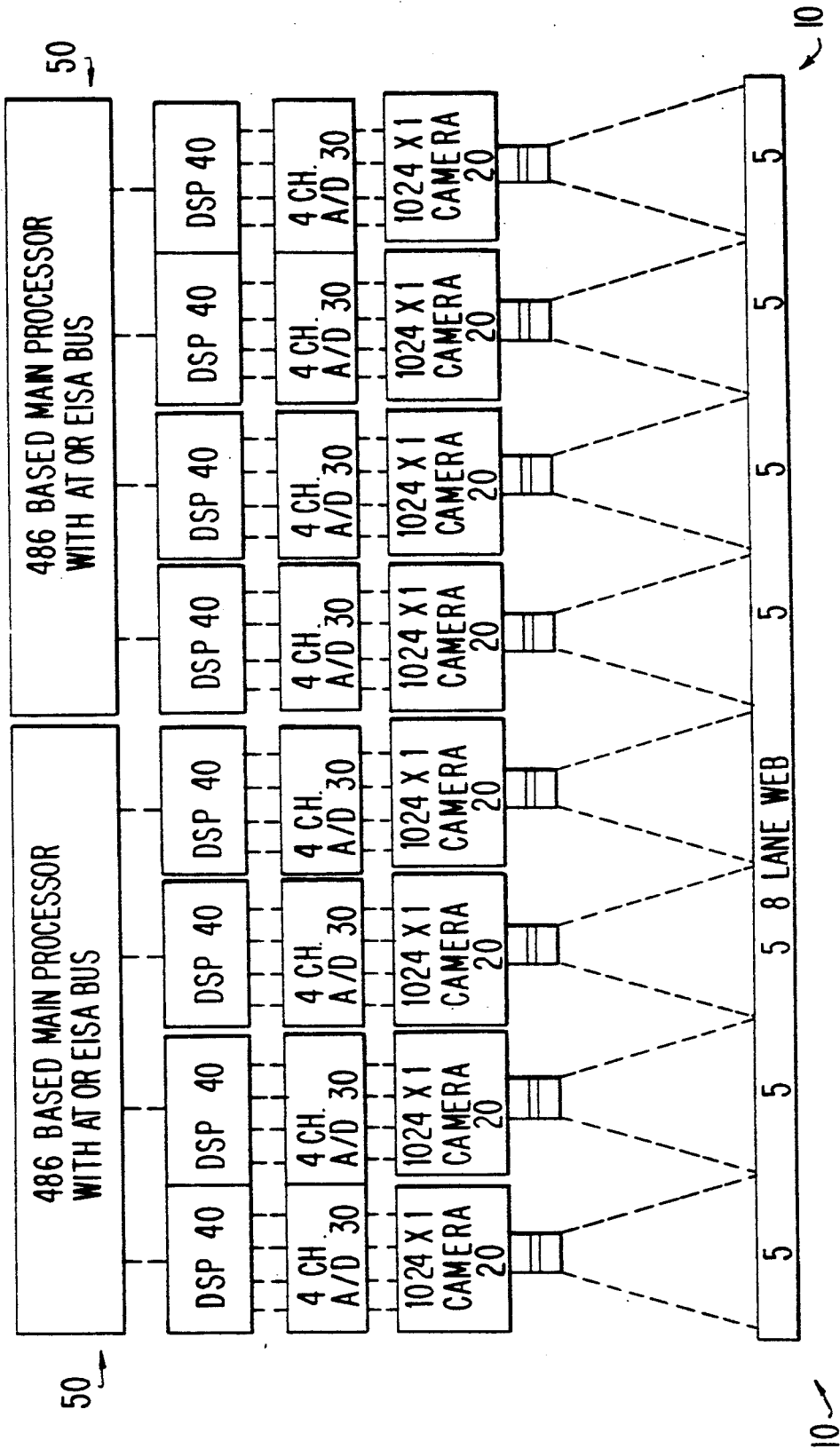
FIG. 1 is block diagram of a preferred embodiment of a modular web inspection system with eight web inspection modules according to the present invention.

The web inspection system of this invention is a linear matrix of inspection modules. Each module inspects a transverse section of printed material. Preferably, each transverse section is an approximately equal section of a printed web. In the case of cigarette packaging, each transverse section, or "lane", might be that part of the width of the web that ultimately forms one row of cigarette packs, the total web being several packs wide. The web passes under the inspection modules at a rate of speed of from about 500 feet per minute to about 1200 feet per minute, which usually matches the velocity at which the printed web is produced by a printing apparatus. The inspection system provides for the real-time detection of defects in each lane of the printed web.

The modular approach provides for maximum flexibility by allowing webs of printed packaging with various numbers of lanes to be inspected without modification of the inspection system. The cigarette packaging industry often prints webs with eight lanes of identical packaging. However, some brands have a different number of lanes. The width of lanes may also vary from product to product and the specificity of flaw detection desired may also vary depending on the quality desired. The modular inspection system allows the user to vary the number of lanes and to vary the degree of specificity of detection by adjusting the width of the web inspected by a single module (this can be done, e.g., by adjusting the distance between the web and the detection module).

The web inspection system of this invention preferably uses the video receptors in a solid-state video camera to create an analog signal representing the amount of light reflected from a single line of the printing web surface. This analog signal is converted into a gray scale digital representation by an analog to digital converter. Thus, each line of the web is represented by a collection of gray scale values; one gray scale value for each pixel on that line. The present embodiment of the invention uses 1024 pixels per line with each pixel represented by an 8-bit 256-level gray scale value, where 0 is black and 255 is white.

The gray scale representation is also converted into a second set of data called the bipolar gray scale gradient representation. The bipolar gray scale gradient data set is created by subtracting the gray scale value of the previous pixel from the current pixel's gray scale value.

The inspection should preferably have a certain degree of resolution in order to adequately detect flaws. The degree of resolution required is dependent on the image to be analyzed and the type of flaws to be detected. In the cigarette packaging industry it has been determined that the preferred resolution is approximately 0.1 millimeter. In the present embodiment the placement of the camera of each module can be adjusted to provide the required resolution. In one application of the present embodiment each of the 1024 pixels corresponds to approximately 0.1 millimeter of the web surface. Thus, the width of each lane is approximately 102.4 millimeters, with each 0.1 millimeter represented by one 8-bit gray scale pixel, for a total of 1 kilobyte of data per line. With the longitudinal resolution equal to the transverse resolution of 0.1 millimeters, 25,400 kilobytes of data are generated every second at a longitudinal web velocity of approximately 500 feet per minute, and 60,960 kilobytes of data are generated every second at a longitudinal web velocity of 1200 feet per minute.

A timing mark is printed on the web at the first print station to alert the microprocessor that the beginning of a new image has occurred on the web. The timing mark in the preferred embodiment is present across the web and can be identified by the microprocessor. A separate timing mark for each repeated pattern is available. The next line of 1024 pixels represents the first line of the actual image in which flaws are to be detected.

A shaft encoder is located in close proximity to the inspection region where it is driven by the moving web or a roller which contacts the web. The shaft encoder in the preferred embodiment sends a Y-bit address component that corresponds to the position of the line of 1024 bytes with respect to the longitudinal axis of the web (DY). A second X-bit address component is generated to identify the position of each pixel within the line of 1024 pixels (DX).

Alternatively, the creation of the X-bit longitudinal address component could be synthesized by using a phase locked loop (PLL) circuit using the timing mark as the source frequency.

The two address components provide the location of the pixel within the image. A gray scale value and address are generated for each pixel and are input to a digital signal processor (DSP) for comparison with the proper value for each pixel of the flawless target image.

One of the difficulties in a pixel by pixel comparison of gray scale values or bipolar gradient gray scale differences is the constant shifting of the image caused by jitter. Jitter is the shifting of the image in both the longitudinal and transverse axes. Longitudinal jitter is a result of a phase change between the web and the shaft encoder, while transverse jitter occurs as the web shifts from side to side under the inspection modules. Since the resolution of image data is often below one millimeter, any amount of jitter in either direction will make it impossible to guarantee alignment of every pixel of the input image with the flawless target image. Comparison of misaligned pixels would result in an incorrect determination that an error is present.

The effect of this jitter must be minimized in order to reduce the number of incorrect flaw determinations. A two dimensional matrix of pixel values is created by the DSP for each input image. In a learning phase each input image is pre-stabilized by the primary processor and then transferred to a non-real-time secondary processor. To prestabilize an image, a pre-selected edge value is searched for at and around a predicted address. The difference between the address at which the edge value is actually located and where it was predicted to have been provides an offset. Both X and Y offsets are generated. These offsets enable the processor to "lock in" on the pre-stabilized image for subsequent pixel address generation. This secondary processor stores each training image and uses multiple training images to build a statistical representation of each pixel's gray scale value or bipolar gray scale gradient.

The secondary processor calculates the minimum value, maximum value, mean and standard deviation for each pixel address. Thus, for each address of an image, a statistical representation of the input values from a set of training images is created. The mean pixel value for each address of the statistical representation of the training image set is compared to the mean pixel value of the same address in the statistical representation of a master training image set in order to create a jitter desensitized template. The mean of the training set should be approximately equivalent to the mean of the master training image set; if it is not, the system signals that human intervention is necessary to determine if there is a problem. Additionally, excess deviation from a threshold indicates excessive jitter that must be dealt with mechanically.

The secondary processor uses the statistical database of pixel values to create the jitter desensitized template, setting high and low limits for each pixel. The high and low limits correspond to various thresholds which are determined according to sensitivity requirements. The high and low limits could be set at the maximum and minimum values for that pixel. Alternatively, the thresholds could be set at a multiple of the standard deviation, $n \cdot \sigma$, where n is typically between 3 and 5. These limit determinations are the same for detection using either gray scale values or bipolar gradient gray scale analysis. The template is then sent to the DSP which then compares incoming images to the template. If the pixel values do not fall within the template limits, the address of the flaw is sent to the secondary processor.

The system can notify the operator and identify the lane of the printed web in which the flaw occurs. Flaws can also be stored in the secondary processor for later analysis. The secondary processor is capable of determining whether flaws are isolated to one lane or are across all lanes.

The comparisons of incoming pixel values with jitter desensitized template values occurs at a sufficient rate of speed in the DSP due to the simplicity of the calculations. The time intensive creation of the training image set and template are done only once per complete printed web. Thus, once the template has been created, the web inspection module can function at the about 500 feet per minute to about 1200 feet per minute rate as required.

The present invention preferably uses no special cameras or hardware components. Thus, the cost of the modular web detection system is kept low. Each module is flexible since each module has a separate training set, so that the image in each lane need not be the same. Similarly, the number of images across a web could be fewer than the number of modules, in which case one or more modules could be disabled and the distance between the printed web and video cameras could be adjusted accordingly, taking into consideration the desired inspection resolution. Each module is also able to pre-stabilize the image in its own lane, reducing the jitter caused by transverse shifts in the web.

A preferred embodiment of an inspection system according to the invention is shown in FIG. 1. A printed web 10 with eight lanes 5 of printed material passes under eight identical video cameras 20. Each video camera 20 is the input to each inspection module which may be either of the preferred embodiments shown in FIG. 2 and 3. Each inspection module is independent in that the distance between the video camera 20 and the printed web 10 may vary without degrading system performance. Furthermore, each inspection module is independent in that a printed web 10 may contain a different number of lanes 5. A module could be disabled and the distance between the video cameras 20 and the printed web 10 could be increased so as to inspect a printed web 10 of the same width that had only seven lanes 5, or some other number less than eight. These modifications must consider the effect on the desired inspection resolution.

Each inspection module has the same video camera 20, analog-to-digital, (A/D) converter 30 and digital signal processor (DSP) 40. Each group of four modules is connected to secondary processor 50 which in this preferred embodiment is an 80486-based personal computer with an AT, EISA, MCA or other industry-standard bus architecture. This embodiment is preferred for cost reasons. Other suitable architectures could also be used such as 68000 series microprocessor based systems.

Figure 2:
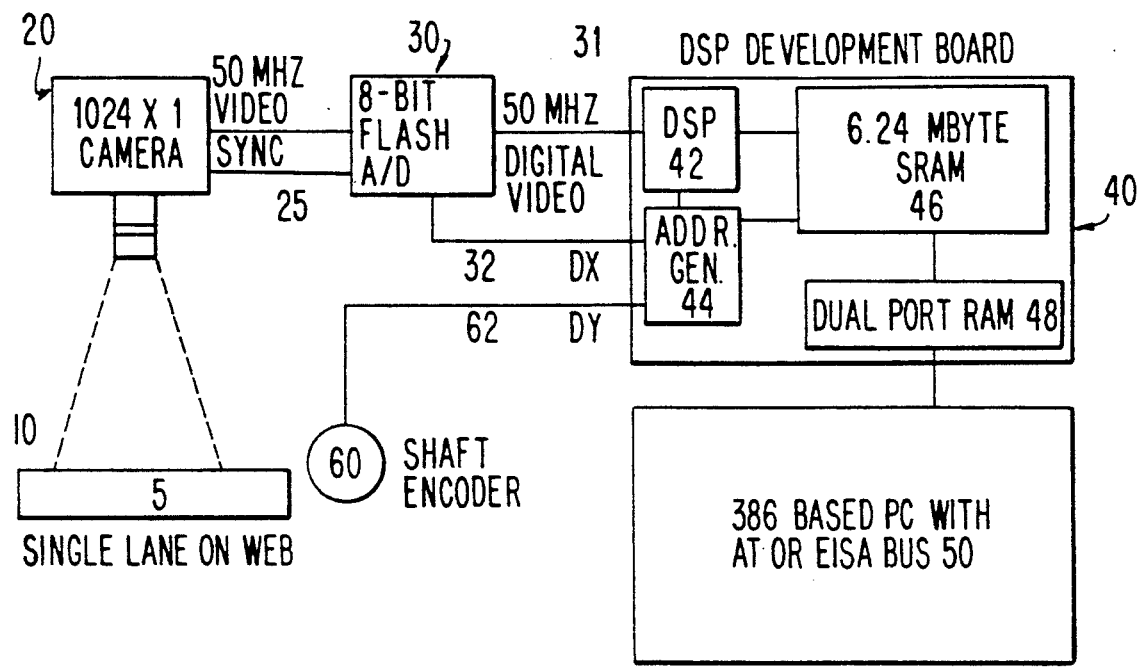
FIG. 2 is a block diagram of a first embodiment of a web inspection module according to the invention for use in the modular web inspection system of FIG. 1.

A first preferred embodiment of an inspection module according to the present invention is shown in FIG. 2. Each lane 5 on the printed web 10 passes under a video camera 20 positioned above the web 10. The video camera 20 is a collection of 1024 photodiodes which convert the light reflected from one line across the web into a set of corresponding 50 MHz analog video signals 25.

These analog signals 25 are sent to an 8-bit flash analog-to-digital (A/D) converter 30 which converts each analog signal 25 into an 8-bit gray scale value. Each 8-bit gray scale value represents one of the 255 possible discrete levels of gray between black at 0 and white at 255. The A/D converter 30 also produces an address (DX) 32 which corresponds to the position of each pixel within the line.

Each line of the web provides 1 kB of data which is then transferred by a 50 MHz bandwidth bus 31 to the digital signal processor (DSP) 42. DSP 42 is resident on a DSP development board 40 which also contains an address generator 44, at least 6.24 megabytes (MB) of static random access memory (SRAM) 46 and a dual port random access memory (RAM) 48. The address generator 44 concatenates the DX address 32 produced by the A/D converter 30, which corresponds to the position of the pixel within a line, with a DY address 62 produced by a shaft encoder 60, which corresponds to location of the line within the two dimensional image matrix.

SRAM 46 is the location of the image template used by DSP 42 for comparisons to the input image. SRAM 46 also stores the initial training images which are then sent to the dual port RAM 48. The dual port RAM 48 permits training images to be sent to a secondary computer 50, which in the preferred first embodiment is an 80386-based personal computer with an AT or EISA bus.

In secondary computer 50 training images from each lane 5 are analyzed and a set of statistical representations for each pixel is developed. Each pixel in the training image set has a statistical mean, minimum value, maximum value and standard deviation calculated. This set of statistical representations is then used by secondary computer 50 to create a jitter desensitized image template with thresholds for acceptable pixel values. Dual port RAM 48 is necessary since image templates created in secondary computer 50 are sent to DSP development board 40 via dual port RAM 48.

The image templates are then used by DSP 42 in comparisons with incoming image data 31 from A/D converter 30. If the pixel value does not fall within the range prescribed by the jitter desensitized image template a defect condition present flag is sent to secondary computer 50. Secondary computer 50 can then either log the error data or alert the operator.

A second preferred embodiment of an inspection module in accordance with the invention is shown in FIG. 3. In the second embodiment an input image 5 printed on a web 10 passes under a video camera 20 containing 1024 photodiodes. The 1024 analog signals which represent the amount of light reflected from the one line of the image are separated into four separate sets 26. Video camera 20 is a multi-tap unit. Each set 26 of analog signals is routed to its respective A/D converter 30. The output 33 from each A/D converter 30 is an 8-bit gray scale representation of a pixel value where 0 is black and 255 is white. Four 8-bit gray scale pixel values in parallel provide a 32-bit word which is then processed by a 32-bit DSP 43 in contrast to the 8-bit DSP 42 in the first preferred embodiment of FIG. 2. As with the first preferred embodiment the same relationship exists between DSP 43 and secondary processor 50.

Figure 4B:
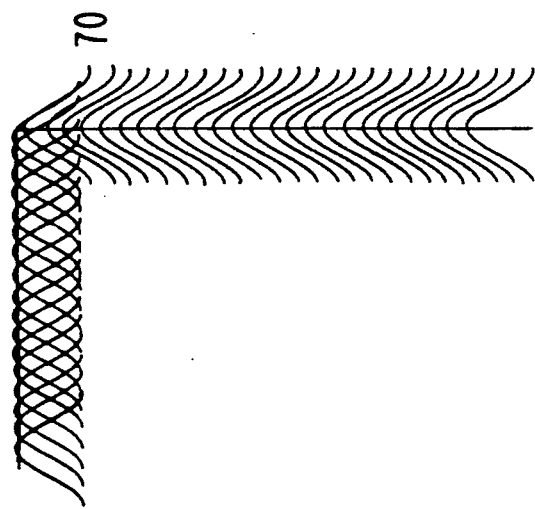
FIG. 4B is a graphic representation of a close up view of the upper right corner of the training image set of FIG. 4A showing a statistical representation of each pixel in the statistical training set.
Figure 4A:
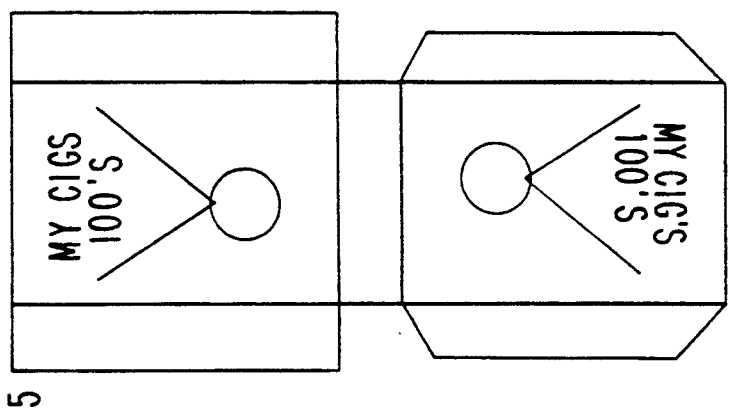
FIG. 4A is a graphic representation of a statistical training set developed to represent the statistical spread of gray scale values for each pixel in a training image set in a web inspection system according to the present invention.

The statistical representation of the training image set is depicted in FIGS. 4A and 4B. Each pixel of each line of printed image lane 5 of FIG. 4A has a corresponding statistical representation 70 shown in FIG. 4B. Statistical representation 70 includes the minimum and maximum, the mean and the standard deviation from the mean of the gray scale values present for each pixel in the set of training images.

Figure 6:
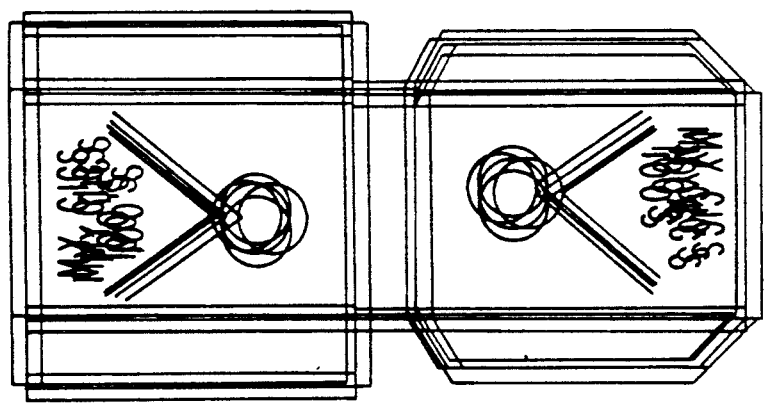
FIG. 6 is a graphic representation of the effect of longitudinal and transverse jitter of the input image of FIG. 5.
Figure 5:
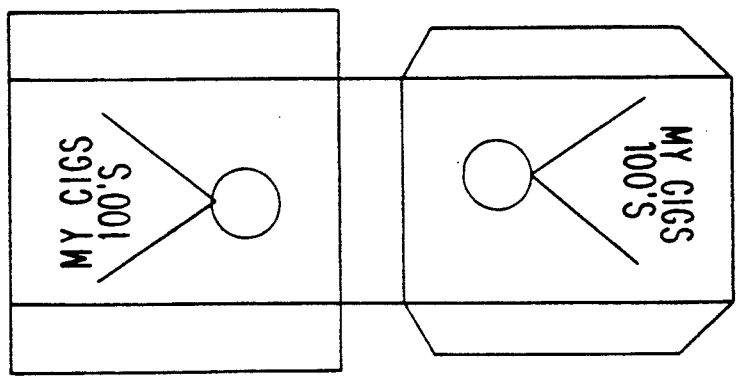
FIG. 5 is a graphic representation of an input image to be inspected in accordance with the present invention.

A graphical representation of an input image present in lane 5 is depicted in FIG. 5. A graphical representation of the effect of movement or jitter of the web on the image is shown in FIG. 6. The image elements of the input image do not appear in the same pixel locations within an input image matrix due to the jitter of the web in both the transverse (x) and longitudinal (y) axes. Thus, if each image were compared to the original input matrix incorrect determinations of flaws would occur.

Figure 7:
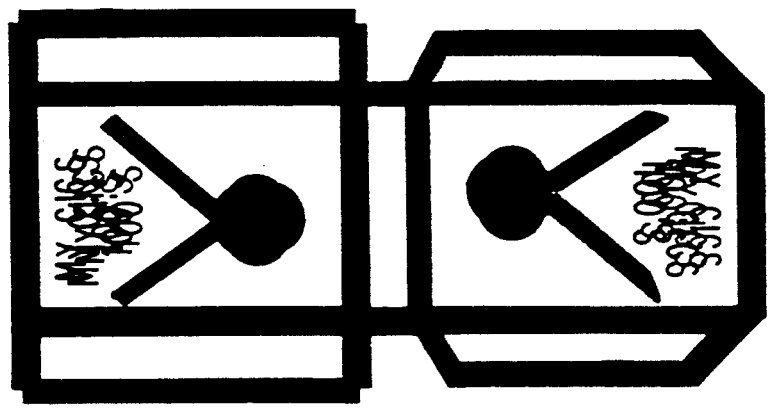
FIG. 7 is a drawing of a template that accounts for the effect of jitter of the input image of FIG. 5.

A jitter desensitized template created from training images in secondary computer 50 is depicted in FIG. 7. The jitter adjusted image is desensitized to occurrence of the image within a certain jitter range. Thus, the number of false flaw determinations is reduced.

Thus, it can be seen that a high speed, high resolution modular web inspection system which detects flaws in a printed web by comparison of input images to a jitter desensitized template created from statistical data gathered from a set of initial training images and compared to a master set of statistical image data is provided. One skilled in the art will appreciate that the present invention can be practiced by other than the described embodiments, which are presented for purposes of illustration and not of limitation, and that the present invention is limited only by the claims which follow.

What is claimed is:

1. For use in a modular system for the inspection of the lanes of a printed web, said system having analog image input means, analog-to-digital conversion means, primary real-time digital signal processing means and secondary non-real-time processing means, a method for detecting flaws in a printed web, said method comprising the steps of:

inputting an analog representation of each pixel of a line of an input image from a printed web;

converting the analog representation to a gray scale digital representation;

transferring the digital representation of each line to the primary digital signal processing means;

generating pre-stabilization offsets for the digital representation in the primary digital signal processing means;

transferring the digital representation of a collection of lines comprising an image to the secondary processing means;

creating in the secondary processing means a statistical representation of the gray scale values for each pixel from a set of input images;

calculating in the secondary processing means the minimum and maximum threshold values for a jitter desensitized template;

transferring the template to the primary digital signal processing means; and comparing input images to the template in the primary digital signal processing means.

2. The method of claim 1 further comprising converting the gray scale digital representation to a bipolar gray scale gradient digital representation.

3. The method of claim 1 further comprising compiling a list of pixel addresses where the pixel values are below the minimum or above the maximum threshold value.

4. The method of claim 3 further comprising providing a signal to the operator that a pixel value is below the minimum or above the maximum threshold value.

5. The method of claim 3 further comprising the steps of:

determining in which lanes of the printed web the pixel values are below the minimum or above the maximum threshold value; and providing a signal to the operator indicating the lanes of the printed web in which pixel values are below the minimum or above the maximum threshold value.

6. A modular web inspection system each module comprising:

means for inputting an analog representation of an image;

means for converting the analog representation to a gray scale digital representation and for generating pre-stabilization offsets for the gray scale digital representation;

a secondary non-real-time processing means for creating a statistical representation of the gray scale values of multiple input images and calculating the minimum and maximum threshold values for a jitter desensitized template;

primary real-time digital signal processing means for the comparison of each pixel value of the input image to the minimum and maximum threshold values for that pixel in the jitter desensitized template; and means for transferring the digital representation between the input means and processing means.

7. The modular web inspection system in claim 6 further including means for converting the gray scale digital representation to a bipolar gray scale gradient digital representation.

8. The modular web inspection system in claim 6 further including means for compiling a list of pixel values below the minimum or above the maximum threshold value.

9. The modular web inspection system in claim 7 further including output means for signalling the operator that a pixel value is below the minimum or above the maximum threshold value.

10. The modular web inspection system in claim 7 further including:

means for determining in which lanes of the printed web the pixels are below the minimum or above the maximum threshold value; and means for providing an output to the operator indicating the lanes of the printed web in which pixel values are below the minimum or above the maximum threshold value.

* * * * *